US012605187B1

(12) United States Patent
Xiao

(10) Patent No.: US 12,605,187 B1
(45) Date of Patent: Apr. 21, 2026

(54) SPERM COLLECTOR

(71) Applicant: Dongguan Buck Medical Technology Co., Ltd., Dongguan (CN)

(72) Inventor: Jianlin Xiao, Guangzhou (CN)

(73) Assignee: Dongguan Buck Medical Technology Co., Ltd., Dongguan (CN)

( * ) Notice: Subject to any disclaimer, the term of this patent is extended or adjusted under 35 U.S.C. 154(b) by 0 days.

(21) Appl. No.: 19/272,624

(22) Filed: Jul. 17, 2025

(30) Foreign Application Priority Data

Dec. 4, 2024 (CN) .......................... 202422978847.9

(51) Int. Cl.
  *A61B 17/43* (2006.01)
  *A61B 17/00* (2006.01)
(52) U.S. Cl.
  CPC .... *A61B 17/43* (2013.01); *A61B 2017/00398* (2013.01); *A61B 2017/00991* (2013.01)
(58) Field of Classification Search
  CPC .......... A61B 17/43; A61B 2017/00398; A61B 2017/00991; A61H 19/00; A61H 2201/00; A61H 19/30; A61H 19/32; A61H 19/50; A61F 5/41
  See application file for complete search history.

(56) References Cited

U.S. PATENT DOCUMENTS

2010/0030116 A1* 2/2010 Chana ..................... A61B 90/06
                                                  600/587
2020/0039599 A1* 2/2020 Chang ..................... B62J 50/22
2023/0012669 A1* 1/2023 Liu ......................... A61H 19/32
2023/0210718 A1* 7/2023 Zhou ...................... A61H 19/32
                                                  600/38
2023/0355466 A1* 11/2023 Cheng ..................... A61F 7/007
2025/0009593 A1* 1/2025 Daley ............... A61H 15/0092

FOREIGN PATENT DOCUMENTS

CN        203935296 U    11/2014
CN        204709070 U    10/2015
CN        109674639 A  *  4/2019    ............. A61H 19/44
CN        219629860 U     9/2023
CN        118078602 A  *  5/2024    ............... A61H 7/00
EP          2163223 B1 *  9/2011    ........... A61D 19/021
WO    WO-2024148681 A1 *  7/2024    ............. A61H 23/02

* cited by examiner

*Primary Examiner* — Alex M Valvis
*Assistant Examiner* — Julie Thi Tran
(74) *Attorney, Agent, or Firm* — Nitin Kaushik

(57) ABSTRACT

Disclosed is a sperm collector, including a sperm collector body, where the sperm collector body includes a sperm collection device, the sperm collector body further includes a gripping portion connected to the sperm collection device, and the gripping portion includes a telescopic member with both ends extending outward from the sperm collector body, and handles arranged at both ends of the telescopic member. The gripping portion is additionally arranged based on the original sperm collection device, and the gripping portion is formed by combining the telescopic member and the handles. During actual operation, the handles achieve a corresponding gripping effect, which reduces collection instability and operational difficulty. The telescopic member in the present disclosure facilitates storage, use of the handles increases a lateral space occupied by the entire sperm collector, and the handles retract inward towards a housing, which solves the problem of inconvenient storage.

4 Claims, 9 Drawing Sheets

52

SPERM COLLECTOR

CROSS-REFERENCE TO RELATED APPLICATIONS

The application claims priority to Chinese patent application No. 202422978847.9, filed on Dec. 4, 2024, the entire contents of which are incorporated herein by reference.

TECHNICAL FIELD

The present disclosure relates to the technical field of artificial insemination, and in particular to a sperm collector.

BACKGROUND

In vitro fertilization (IVF) is an assisted reproductive technology used to help couples or individuals suffering from infertility to achieve the desire for pregnancy. In the IVF process, sperms are usually collected manually from males, and then combined with female oocytes for in vitro fertilization.

In this process, a sperm collector (or a semen collector) as a critical tool is used to assist a medical professional or laboratory technician in collecting semen samples from males. The semen samples are subsequently processed and screened to ensure that the highest-quality sperm is used for fertilization. A conventional sperm collector is specially designed to ensure safe and comfortable sperm collection and minimize adverse effects of environmental and technical factors on sperm quality.

However, the conventional sperm collector is not provided with a corresponding gripping portion, and lack of a handle may require a male user to be more cautious during operation, such that the sperm collector is easily tilted due to instability of gripping. Particularly during the collection process, improper hand movements may lead to tilting of the sperm collector or semen spillage. Such instability may affect smooth sperm collection and increase operational difficulty.

SUMMARY

In order to solve the above problems, including the problem of instable sperm collection caused by improper actions, the present disclosure provides a sperm collector with a corresponding gripping structure.

To achieve the above objective, the present disclosure adopts the following technical solution: a sperm collector includes a sperm collector body, and the sperm collector body includes a sperm collection device, where the sperm collector body further includes a gripping portion connected to the sperm collection device, and the gripping portion includes a telescopic member with both ends extending outward from the sperm collector body, and handles arranged at both ends of the telescopic member.

In the present disclosure, the gripping portion is additionally arranged based on the original sperm collection device, and the gripping portion is formed by combining the telescopic member and the handles. During actual operation, the handles achieve a corresponding gripping effect, which reduces collection instability and operational difficulty.

Use of the telescopic member in the present disclosure facilitates storage, use of the handles increases a lateral space occupied by the entire sperm collector, and under the action of the telescopic member, the handles retract inward towards a housing, which solves the problem of inconvenient storage.

Further, the telescopic member includes a drive motor, a drive gear, and racks, the handles are internally hollow, an inner end of either of the handles is provided with an opening, the racks are fixed inside the handles, the drive gear is sleeved on a motor shaft of the drive motor, the drive gear is located between the two handles, and the drive gear is meshed with the racks that penetrate through the opening; and according to the above technical solution, driving of the racks mainly aims to enhance stability and accuracy of the sperm collector, and the racks, under the action of the drive motor, press against inner walls of outer ends of the handles, such that the handles extend outward.

In this example, the racks are distributed above and below the drive gear and meshed with the drive gear, and the racks are symmetrically arranged relative to each other; and such arrangement mainly aims to reduce the number of drive motors required, and the meshed engagement between the drive gear and two racks further improves synchronization during extension and retraction.

Further, the sperm collector further includes a rotary encoder and adjustment knobs corresponding to the handles in quantity (in this example, numbers of the adjustment knobs and the handles are both two), the rotary encoder and the adjustment knobs are sleeved on the handles, the adjustment knobs are connected to an input end of the rotary encoder (the input end of the rotary encoder rotates), an output end of the rotary encoder is connected to a control circuit board, the control circuit board is electrically connected to the sperm collection device, and the adjustment knobs are rotatably arranged on the handles, which mainly facilitates hierarchical adjustment during sperm collection, such that an operating speed of the sperm collection device may be accordingly adjusted. (In this example, the number of the rotary encoders is one, but based on actual conditions, the number of the rotary encoders is alternatively two.)

Further, the sperm collector body includes a housing and a guide assembly located inside the housing, and when the telescopic member is in a retracted state, the adjustment knobs are located inside the housing, and the guide assembly plays a guiding effect, and enhances stability of the adjustment knobs and the handles when they extend from the housing; and the guide assembly includes a guide rod and a guide sleeve, the guide rod is fixed inside the housing, the guide sleeve is sleeved on both the handles and the guide rod, the adjustment knobs are sleeved on the handles, a limit groove is formed on an inner ring face of either of the adjustment knobs, and a sleeve ring is sleeved on a circumferential face of either of the handles; the limit groove provides a sufficient depth for the sleeve ring to move, and in other words, when the handles are driven to move, the sleeve ring pushes against any side face of the limit groove, which causes a linear telescopic action of the adjustment knob; such design primarily aims to control a motion trajectory of the guide sleeve, the guide sleeve occupies a relatively large space and is connected with the guide rod and the handles; and limited space of the housing, and a smaller motion trajectory of the guide sleeve avoids interference with the drive gear.

Additionally, it is to be noted that, the rotary encoder is fixed to the guide sleeve, and the guide sleeve provides a specific positioning effect for the rotary encoder.

Further, the guide assembly further includes rollers and mounting bases, and the mounting bases are fixed inside the housing and sleeved onto the guide rod; in this example, the number of the mounting bases is two, the rollers are arranged on the mounting bases in a vertically symmetrical manner, a portion of the rack protrudes from an inner end of the handle, and the rollers abut against back faces of the racks, and the back faces of the racks are smooth; the two rollers provide corresponding support to the racks, such that two racks sandwich the drive gear; and such design not only maintains stable meshed engagement between the racks and the drive gear, but also ensures full tooth engagement, and avoids any significant deviation between actual and theoretical positions.

The sperm collector and the control circuit board both belong to prior art, and operational principles and structures thereof will not be described in detail herein.

DETAILED DESCRIPTION OF THE EMBODIMENTS

Figure 1:
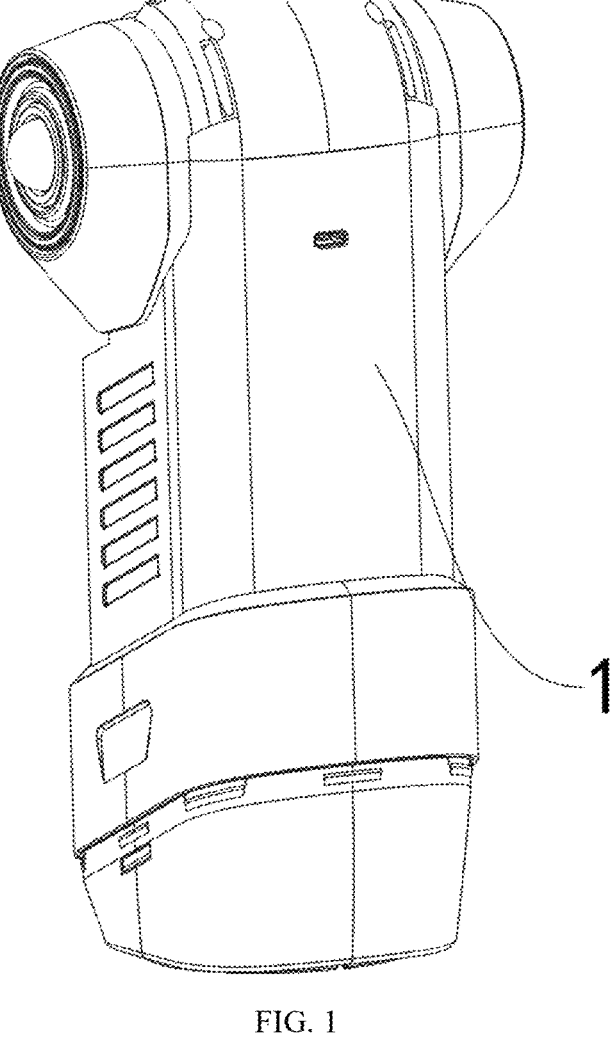
FIG. 1 is a perspective view of the present disclosure.
Figure 2:
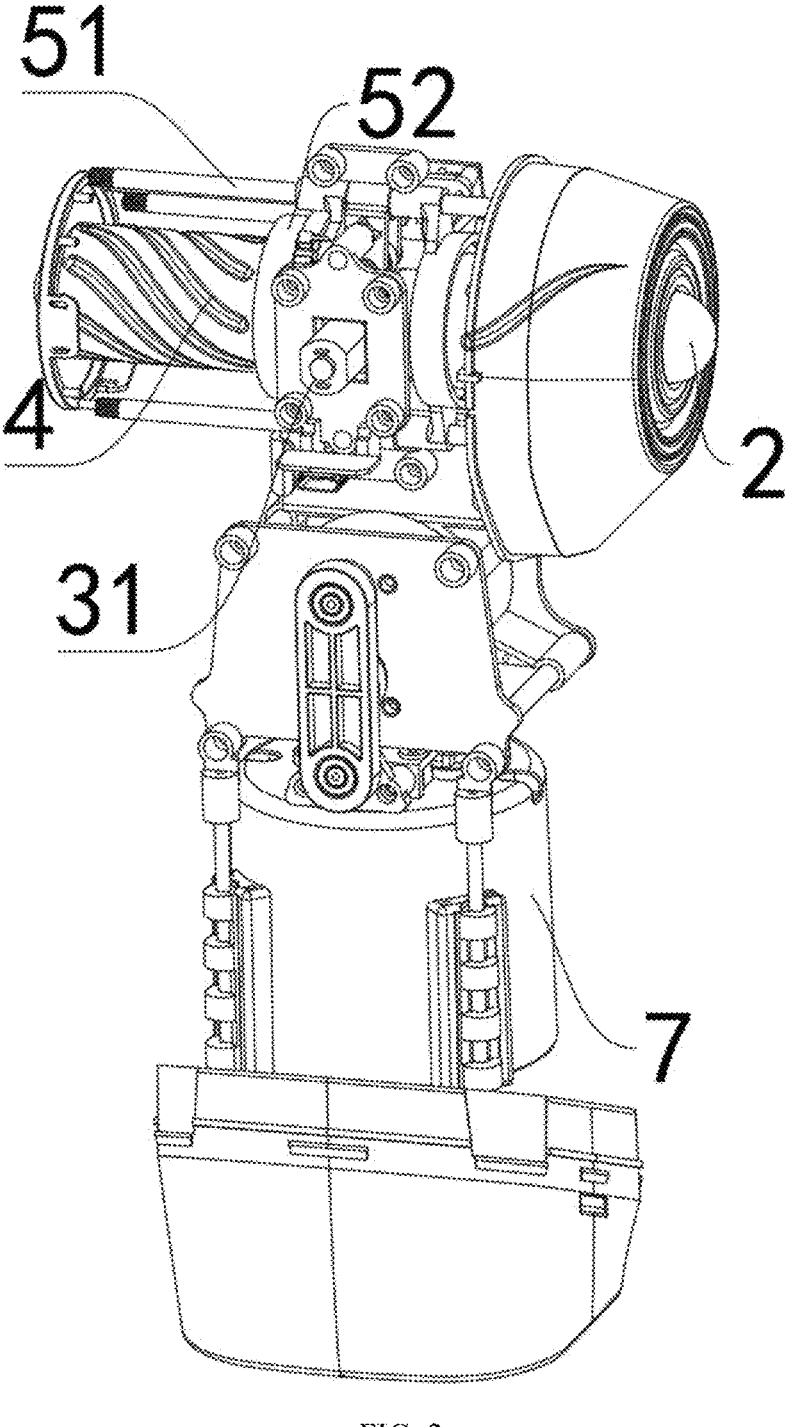
FIG. 2 is a perspective view of the present disclosure with a portion of a housing in FIG. 1 hidden.
Figure 3:
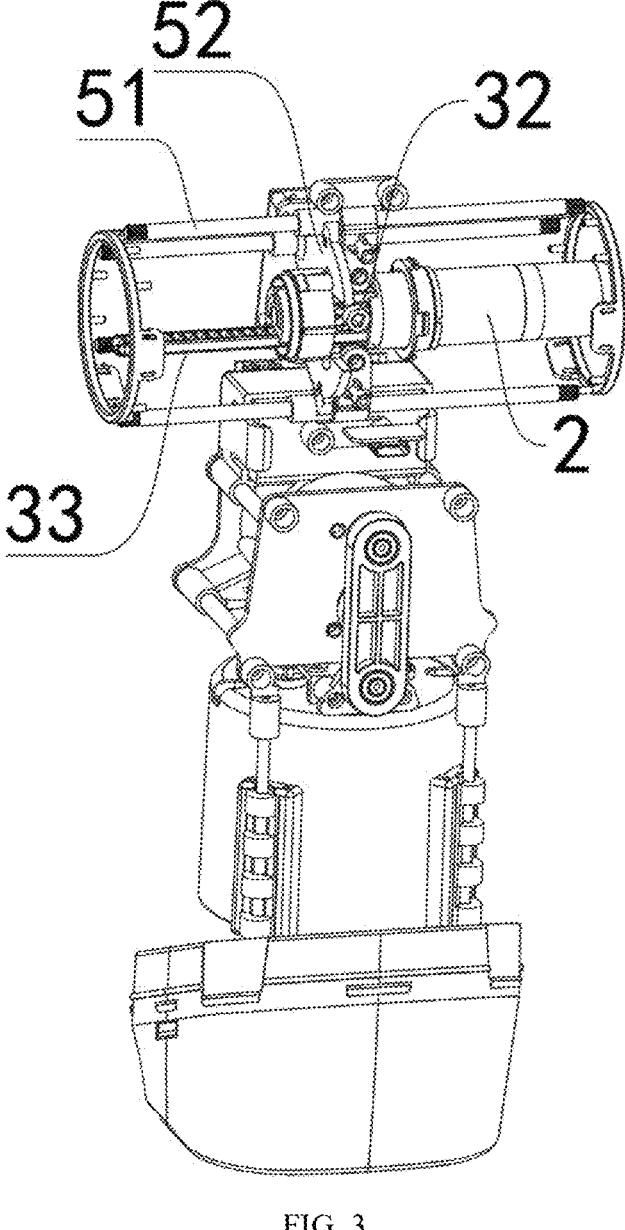
FIG. 3 is a perspective view of the present disclosure with any handle hidden.
Figure 4:
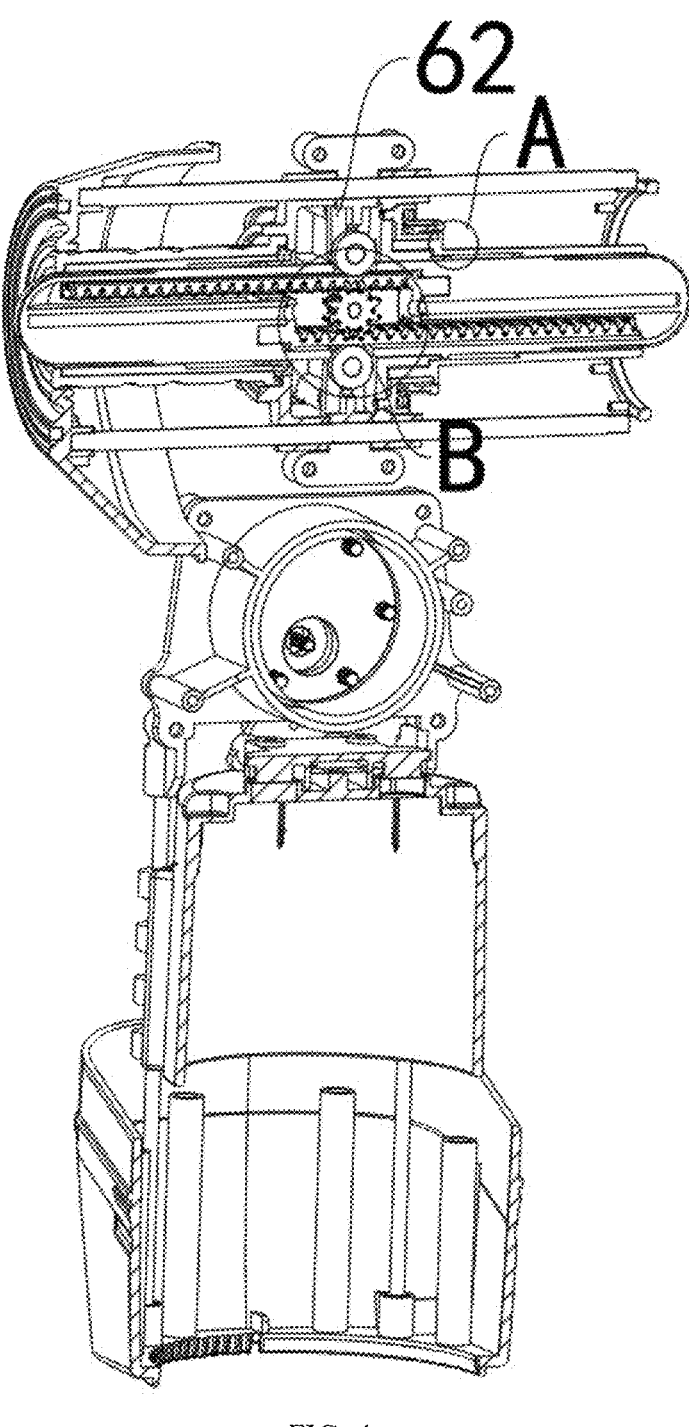
FIG. 4 is a sectional view of the present disclosure.
Figure 5:
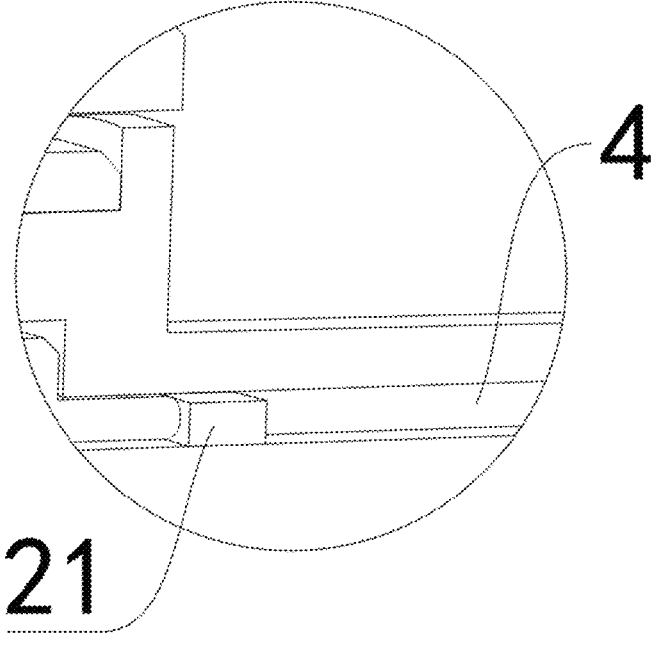
FIG. 5 is an enlarged schematic diagram of a portion A in FIG. 4.
Figure 6:
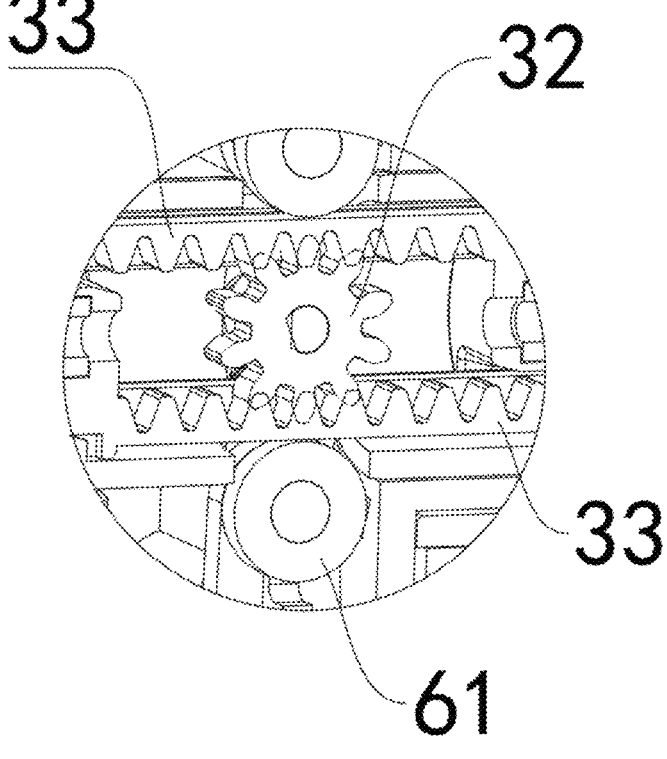
FIG. 6 is an enlarged schematic diagram of a portion B in FIG. 4.
Figure 7:
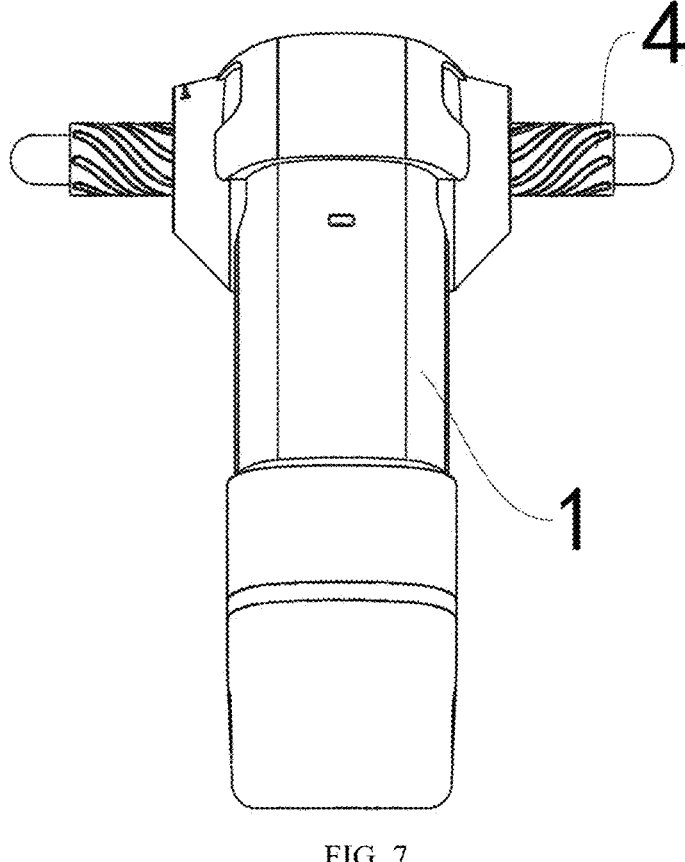
FIG. 7 is a use state diagram of the present disclosure.
Figure 8:
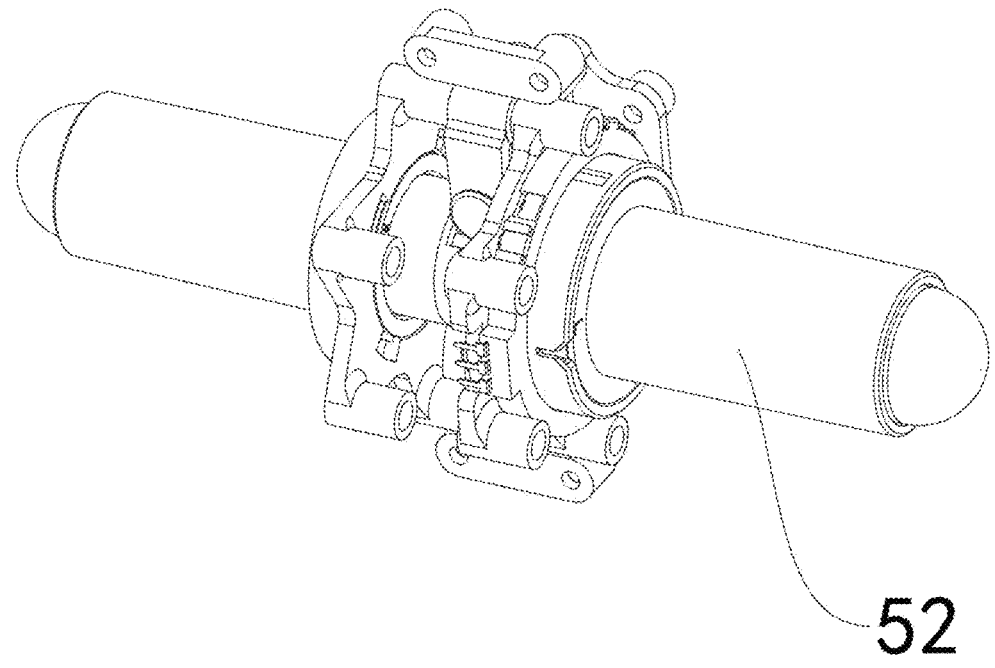
FIG. 8 is a diagram of an internal structure of the present disclosure.
Figure 9:
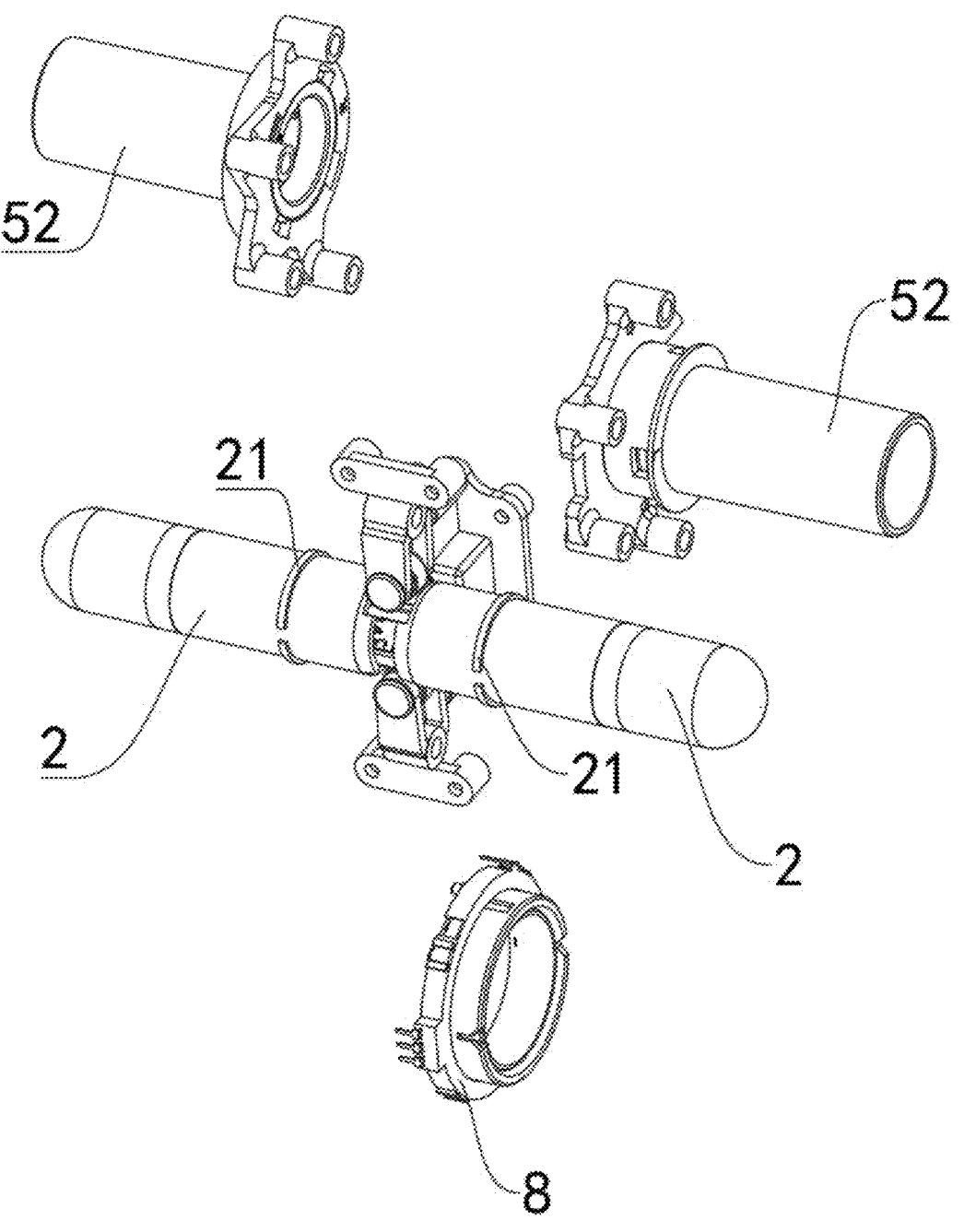
FIG. 9 is an exploded view of FIG. 8.

As shown in FIGS. 1-9, a sperm collector includes a sperm collector body, and the sperm collector body includes a sperm collection device 7, where the sperm collector body further includes a gripping portion connected to the sperm collection device 7, and the gripping portion includes a telescopic member with both ends extending outward from the sperm collector body, and handles 2 arranged at both ends of the telescopic member.

In the present disclosure, the gripping portion is additionally arranged based on the original sperm collection device 7, and the gripping portion is formed by combining the telescopic member and the handles. During actual operation, the handles 2 achieve a corresponding gripping effect, which reduces collection instability and operational difficulty.

Use of the telescopic member in the present disclosure facilitates storage, use of the handles 2 increases a lateral space occupied by the entire sperm collector, and under the action of the telescopic member, the handles 2 retract inward towards a housing 1, which solves the problem of inconvenient storage.

Further, the telescopic member includes a drive motor 31, a drive gear 32, and racks 33, the handles 2 are internally hollow, an inner end of either of the handles 2 is provided with an opening, the racks 33 are fixed inside the handles 2, the drive gear 32 is sleeved on a motor shaft of the drive motor 31, the drive gear 32 is located between the two handles 2, and the drive gear 32 is meshed with the racks 33 that penetrate through the opening; and according to the above technical solution, driving of the racks 33 mainly aims to enhance stability and accuracy of the sperm collector, and the racks 33, under the action of the drive motor 31, press against inner walls of outer ends of the handles 2, such that the handles 2 extend outward.

In this example, the racks 33 are distributed above and below the drive gear 32 and meshed with the drive gear 32, and the racks 33 are symmetrically arranged relative to each other; and such arrangement mainly aims to reduce the number of drive motors required, and the meshed engagement between the drive gear 32 and two racks 33 further improves synchronization during extension and retraction.

Further, the sperm collector further includes a rotary encoder 8 and adjustment knobs 4 corresponding to the handles 2 in quantity (in this example, numbers of the adjustment knobs 4 and the handles 2 are both two), the rotary encoder 8 and the adjustment knobs 4 are sleeved on the handles 2, the adjustment knobs 4 are connected to an input end of the rotary encoder 8 (the input end of the rotary encoder 8 rotates), an output end of the rotary encoder 8 is connected to a control circuit board, the control circuit board is electrically connected to the sperm collection device 7, and the adjustment knobs 4 are rotatably arranged on the handles 2, which mainly facilitates hierarchical adjustment during sperm collection, such that an operating speed of the sperm collection device 7 may be accordingly adjusted. (In this example, the number of the rotary encoders is one, but based on actual conditions, the number of the rotary encoders is alternatively two.)

Further, the sperm collector body includes a housing 1 and a guide assembly located inside the housing 1, and when the telescopic member is in a retracted state, the adjustment knobs 4 are located inside the housing 1, and the guide assembly plays a guiding effect, and enhances stability of the adjustment knobs 4 and the handles 2 when they extend from the housing 1; and the guide assembly includes a guide rod 51 and a guide sleeve 52, the guide rod 51 is fixed inside the housing 1, the guide sleeve 52 is sleeved on both the handles 2 and the guide rod 51, the adjustment knobs 4 are sleeved on the handles 2, a limit groove 41 is formed on an inner ring face of either of the adjustment knobs 4, and a sleeve ring 21 is sleeved on a circumferential face of either of the handles 2; the limit groove 41 provides a sufficient depth for the sleeve ring 21 to move, and in other words, when the handles 2 are driven to move, the sleeve ring 21 pushes against any side face 41-$a$ of the limit groove 41, which causes a linear telescopic action of the adjustment knob 4; such design primarily aims to control a motion trajectory of the guide sleeve 52, the guide sleeve 52 occupies a relatively large space and is connected with the guide rod 51 and the handles 2; and limited space of the housing 1, and a smaller motion trajectory of the guide sleeve 52 avoids interference with the drive gear 32.

Additionally, it is to be noted that, the rotary encoder 8 is fixed to the guide sleeve 52, and the guide sleeve 52 provides a specific positioning effect for the rotary encoder 8.

Further, the guide assembly further includes rollers 61 and mounting bases 62, and the mounting bases 62 are fixed inside the housing 1 and sleeved onto the guide rod 51; in this example, the number of the mounting bases 62 is two, the rollers 61 are arranged on the mounting bases 62 in a vertically symmetrical manner, a portion of the rack 33 protrudes from an inner end of the handle 2, and the rollers 61 abut against back faces of the racks 33, and the back faces of the racks 33 are smooth; the two rollers 61 provide corresponding support to the racks 33, such that two racks 33 sandwich the drive gear 32; and such design not only maintains stable meshed engagement between the racks 33 and the drive gear 32, but also ensures full tooth engagement, and avoids any significant deviation between actual and theoretical positions.

The sperm collector and the control circuit board both belong to prior art, and operational principles and structures thereof will not be described in detail herein.

The above implementation modes merely describe the preferred embodiments of the present disclosure, and are not intended to limit the scope of the present disclosure. Without departing from the design spirit of the present disclosure, various modifications and improvements of the technical solution of the present disclosure made by those of ordinary skill in the art should fall within the scope of protection determined in the claims of the present disclosure.

What is claimed is:

1. A sperm collector, comprising a sperm collector body, wherein the sperm collector body comprises a sperm collection device, the sperm collector body further comprises a gripping portion connected to the sperm collection device, and the gripping portion comprises a telescopic member with both ends of the telescopic member extending outward from the sperm collector body, and handles arranged at both ends of the telescopic member;

the telescopic member comprises a drive motor, a drive gear, and racks, wherein the handles are internally hollow, an inner end of either of the handles is provided with an opening, the racks are fixed inside the handles, the drive gear is sleeved on a motor shaft of the drive motor, the drive gear is located between the two handles, and the drive gear is meshed with the racks that penetrate through the opening;

the sperm collector body comprises a housing and a guide assembly located inside the housing, wherein the guide assembly comprises a guide rod and a guide sleeve, the guide rod is fixed inside the housing, the guide sleeve is sleeved on the handles and the guide rod, the adjustment knobs are sleeved on the handles, a limit groove is formed on an inner ring face of either of the adjustment knobs, a sleeve ring is sleeved on a circumferential face of either of the handles, and the rotary encoder is fixed to the guide sleeve.

2. The sperm collector according to claim 1, wherein the racks are distributed above and below the drive gear and meshed with the drive gear, and the racks are symmetrically arranged relative to each other.

3. The sperm collector according to claim 1, further comprising a rotary encoder and adjustment knobs corresponding to the handles in quantity, wherein the rotary encoder and the adjustment knobs are sleeved on the handles, and the adjustment knobs are connected to an input end of the rotary encoder.

4. The sperm collector according to claim 1, wherein the guide assembly further comprises rollers and mounting bases, wherein the mounting bases are fixed inside the housing and sleeved onto the guide rod; the rollers are arranged on the mounting bases in a vertically symmetrical manner, a portion of the rack protrudes from an inner end of the handle, and the rollers abut against beck faces of the racks, and the back faces of the racks are smooth; and the two rollers provide corresponding support to the racks, such that two racks sandwich the drive gear.

\* \* \* \* \*